US00PP23000P2

(12) United States Plant Patent
Egger

(10) Patent No.: US PP23,000 P2
(45) Date of Patent: Aug. 28, 2012

(54) ***KNIPHOFIA* PLANT NAMED 'EMBER GLOW'**

(50) Latin Name: ***Kniphofia* spp.**
Varietal Denomination: Ember Glow

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 13/066,157

(22) Filed: Apr. 6, 2011

(51) Int. Cl.
*A01H 5/00* (2006.01)

(52) U.S. Cl. ..... Plt./443

(58) Field of Classification Search ..... Plt./443
See application file for complete search history.

*Primary Examiner* — Annette Para
(74) *Attorney, Agent, or Firm* — Klarquist Sparkman, LLP

(57) ABSTRACT

A new and distinct *Kniphofia* plant characterized by its massive blooming from August through September, compact habit with multiple crowns, narrow, grassy leaves, bicolor orange and yellow flowers, and excellent vigor.

1 Drawing Sheet

Botanical denomination: *Kniphofia* spp.
Cultivar designation: 'Ember Glow'.

BACKGROUND OF THE INVENTION

The present invention relates to a new and distinct *Kniphofia*, and given the cultivar name is 'Ember Glow'. *Kniphofia* is in the family Asphodelaceae. 'Ember Glow' is a hybrid resulting from a planned breeding program to produce compact, reblooming *Kniphofia*. The cross was made using the following proprietary, unreleased plants: *Kniphofia* K10-1, as the seed parent, and *Kniphofia* K10-2, as the pollen parent. It was selected for best habit, flower color, reblooming, and crown count from many seedlings of the cross in Canby, Oreg.

Compared to *Kniphofia* 'Bressingham Comet' (an unpatented plant), the new cultivar flowers massively in late summer and fall rather than sporadically through the summer. The inflorescences of the new cultivar are bicolor orange and yellow rather than red and yellow.

Compared to *Kniphofia* 'Fire Glow', U.S. Plant patent application Ser. No. 13/066,148, the new cultivar has inflorescences that are bicolor orange and yellow rather than red and yellow.

SUMMARY OF THE INVENTION

The new cultivar is unique and characterized by:

1. massive blooming from August through September in Canby, Oreg.
2. compact habit with multiple crowns
3. narrow, grassy leaves
4. bicolor orange and yellow flowers
5. excellent vigor This new cultivar has been reproduced only by asexual propagation (division, tissue culture). Each of the progeny exhibits identical characteristics to the new cultivar. Asexual propagation by leaf cuttings, tissue culture, and division using standard techniques as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows a plant of a two-year-old *Kniphofia* 'Ember Glow' in the ground in the trial field in September in Canby, Oreg.

DETAILED PLANT DESCRIPTION

The following is a detailed description of the new *Kniphofia* cultivar based on observations one gallon size, nine month old specimens grown from tissue culture, grown outside in part sun in Canby, Oreg. The color descriptions are all based on The Royal Horticultural Society Colour Chart, 5$^{th}$ edition.

Plant:
- *Type*.—Rhizomatous herbaceous perennial.
- *Hardiness*.—USDA Zones 6 to 9.
- *Size*.—Grows to 34 cm wide and 36 cm tall from the top of the soil to the top of the foliage.
- *Crown #*.—About 18.
- *Form*.—Upright and clumping.

Leaf:
- *Type*.—Simple.
- *Shape*.—Strap-like.
- *Arrangement*.—Basal rosette.
- *Blade size*.—Grows to 45 cm long and 10 mm wide.
- *Margins*.—Entire.
- *Apex*.—Acuminate.
- *Base*.—Clasping.
- *Surface texture*.—Glabrous on both surfaces.
- *Venation*.—Parallel.
- *Color*.—Top and bottom side closest to Green 137A.

Inflorescence:
- *Type*.—Spike-like scapose raceme.
- *Number of flowers per raceme*.—About 70.
- *Inflorescence*.—13 cm long and 5.7 cm wide.
- *Peduncle description*.—Grows to 35 cm long and 6 mm wide, glabrous, Yellow Green 146C.
- *Pedicle description*.—2.5 mm long, glabrous, Yellow Green 152D.

*Bloom time*.—August through September in Canby, Oreg.

*Lastingness*.—An inflorescence lasts for 2 to 4 weeks depending on the temperature.

Flower bud:

*Size*.—28 mm long and 4 mm wide.

*Shape*.—Cylindrical.

*Surface texture*.—Glabrous.

*Color*.—Top, Orange Red 31A to Yellow 8C on bottom ⅓; bottom Yellow 8C tinted Orange Red 31A on tip half.

Flower:

*Type*.—Actinomorphic.

*Shape*.—Cylindrical and tubular.

*Size*.—Grows to 30 mm deep and 6.5 mm wide.

*Surface texture*.—Glabrous inside and outside.

*Corolla description*.—6 lobed fused tepals, 28 mm long and 6.5 mm wide, tube 25 mm long and 5 mm wide, lobes reflex, each 2.5 mm wide and 2.5 mm long, shape ovate, margin entire, tip acute; outside and inside color Yellow 10B with top side upper half tinted Orange Red 31 A; older flowers Yellow 10A.

*Pistil description*.—One, 20 mm long, ovary 3 mm long 2.5 mm wide, Yellow Green 144A, style 12 mm long, Green Yellow 1C, stigma White 155A.

*Stamen*.—6, 24 mm long, filaments 23 mm long, and Green White 1D, anthers 1.5 mm long and Greyed Orange 163A, pollen Yellow Orange 14C.

*Fragrance*.—None.

*Fruit and seed*.—None seen.

Pest and diseases: Pests and diseases are infrequent on *Kniphofia* spp. No problems have been observed on this plant grown under commercial conditions in Canby, Oreg.

I claim:

1. A new and distinct *Kniphofia* plant as herein shown and described.

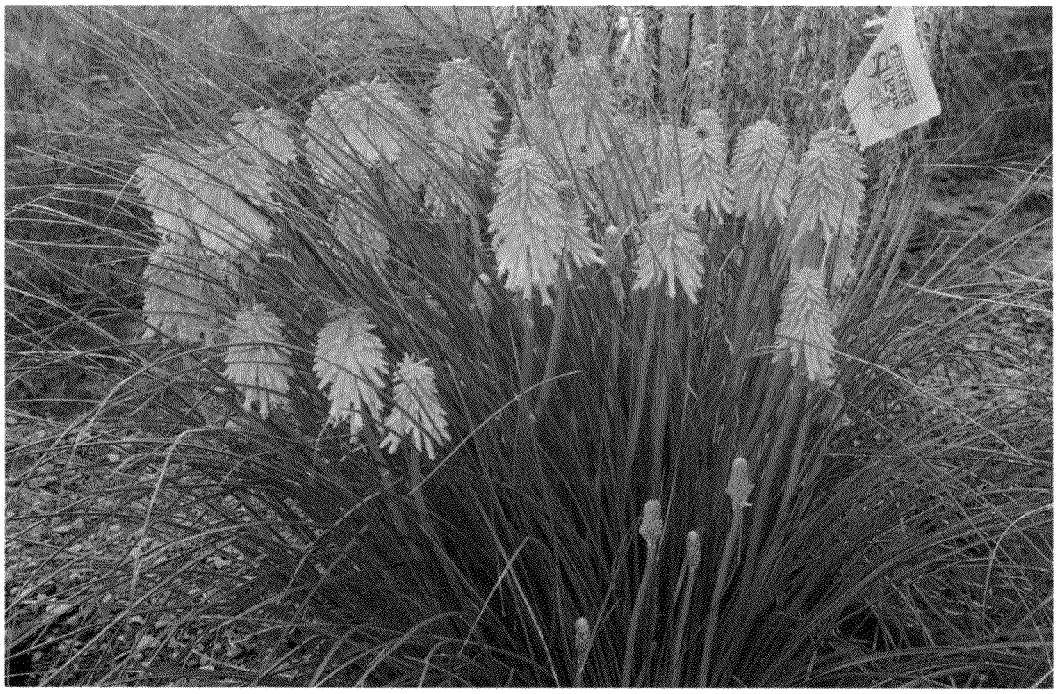

* * * * *